US008715752B2

(12) United States Patent (10) Patent No.: US 8,715,752 B2
Heaton et al. (45) Date of Patent: *May 6, 2014

(54) COMPOSITIONS FOR INCREASING HUMAN GROWTH HORMONE LEVELS

(71) Applicant: Quality IP Holdings, LLC, Carson City, NV (US)

(72) Inventors: Amy L Heaton, Salt Lake City, UT (US); Mitchell K Friedlander, Salt Lake City, UT (US); Dennis Gay, Salt Lake City, UT (US)

(73) Assignee: Quality IP Holdings, Inc., Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,117

(22) Filed: Sep. 20, 2012

(65) Prior Publication Data

US 2014/0079831 A1 Mar. 20, 2014

(51) Int. Cl.
*A61K 36/55* (2006.01)
*A61K 36/00* (2006.01)
*A61K 47/00* (2006.01)
*A61K 9/14* (2006.01)
*A61K 9/00* (2006.01)

(52) U.S. Cl.
USPC ........... 424/745; 424/725; 424/774; 424/439; 424/489; 424/400

(58) Field of Classification Search
None
See application file for complete search history.

(56) References Cited

PUBLICATIONS

Website document entitled "Growth Hormone: Amino Acids as GH Secretagogues" (available at http://www.vrp.com/amino-acids/growth-hormone-amino-acids-as-gh-secretagogues-a-review-of-the-literature?utm_source=RSStwitterfeed&utm_medium=twitter). Downloaded from website Apr. 8, 2013.*
Fung et al. (2002) J. Clin. Pharmacol. 42: 30-36.*
Sen (1999) Molecular and Cellular Biochemistry 196, 31-42.*
Leelarungrayub et al. (2011) Oxidative Medicine and Cellular Longevity. Volum 2011, Article ID 329643.*
Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.
Albert et al.; Low-Dose Recombinant Human Growth Hormone as Adjuvant Therapy of Lifestyle Modifications in the Management of Obesity; Journal of Clinical Endocrinology & Metabolism 89(2) 695-704; 2004.
Bernardi et al.; Somatotropic axis and body weight in pre-menopausal and post-menopausal women: evidence for a neuroendocrine derangement, in absence of changes of insulin-like growth factor binding protein concentrations; Human Reproduction vol. 12, No. 2 pp. 279-287, 1998.

Bidlingmaier et al.; Growth Hormone; Handbook of Experimental Pharmacology 195; 2010; pp. 187-200.
Bjorntorp, et al.; Hypothalamic Origin of the Metabolic Syndrome X; Annals New York Academy of Sciences, pp. 297-307; 1999.
Bjorntorp, P.; Do Stress reactions cause abdominal obesity and comorbidities?; The International Association for the Study of Obesity, Obesity reviews; 2 73-85; 2001.
Bjorntorp, P.; The regulation of adipose tissue distribution in humans; International Journal of Obesity (1996) 20, 191-302.
Blackman et al.; Growth Hormone and Sex Steroid Administration in Healthy Aged Women and Men A Randomized Controlled Trial; JAMA, Nov. 12, 2002—vol. 288, No. 18; pp. 2282-2292.
Bredella, et al.; Peak Growth Hormone-Releasing Hormone-Arginine-Stimulated Growth Hormone iS Inversely Associated with Intramyocellular and Intrahepatic Lipid Content in Premenopausal Women with Obesity; J. Clin Endrocrinol Metab. Oct. 2009; 94(10): 3995-4002.
Carli et al.; Changes in the exercise-induced hormone response to branched chain amino acid administration; Eru. J. Appl. Physiology (1992) 64:272-277.
Chromiak et al.; Use of Amino Acids as Growth Hormone-Releasing Agents by Athletes; Nutrition 18:657-661, 2002.
Corpas et al.; Human Growth Hormone and Human Aging; Endocrine Reviews, vol. 14, No. 1; 1993; pp. 20-39.
Corpas et al.; Oral Arginine-Lysine Does not Increase Growth Hormone or Insulin-like Growth Factor-I in Old Men; Journal of Gerontology: 1993, vol. 48, No. 4, M128-M133.
Ding et al.; Novel serum protein biomarkers indicative of growth hormone doping in healthy human subjects; Preteomics 2011, 11, 3565-3571.
Fogelholm et al. Low-Dose Amino Acid Supplementation: No Effects on Serum Human Growth Hormone and Insulin in Male Weightlifters; International Journal of Sport Nutrition, 1993, 3, 290-297.
Gourmelen et al., Effet du chlorhydrate d'ornithine sur le taux plamatique de l'hormone de croissance (HGH); Annels D'Endocrinologie; pp. 526-528; 1972.
Hayes et al.; Recombinant Human Growth Hormone and Recombinant Human Insulin-Like Growth Factor I Diminish the Cataboloic Effects of Hypogonadism in Man: Metabolic and Molecular Effects; The Journal of Clinical Endocrinology & Metabolism; vol. 86, No. 5; 2001.
Hersch et al.; Growth hormone (GH)-releasing hormone and GH secretagogues in normal aging: Fountain of Youth or Pool of Tantalus?, Clinical Interventions in Aging 2008:3(1) 121-129.
Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088, 1991.
Isidori et al.; A Study of growth hormone release in man after oral administration of amino acids; Current Medical Research and Opinion; vol. 7, No. 7, 1981; pp. 475-481.
Karlsson et al.; Effects of growth hormone treatment on the leptin system and on energy expenditure in abdominally obese men; European Journal of Endocrinology (1998) 138 408-414.
Kraemer et al.; Chronic Resistance training in women potentiates growth hormone in vivo bioactivity: characterization of molecular mass variants; Am. J. Physiol Endocrinol Metab 291: E1177-E1187, 2006.

(Continued)

*Primary Examiner* — Chris R Tate
*Assistant Examiner* — Russell Fiebig
(74) *Attorney, Agent, or Firm* — TraskBritt, P.C.

(57) ABSTRACT

Embodiments of the invention generally relate to supplements for increasing human growth hormone (hGH) levels in healthy human beings.

6 Claims, 1 Drawing Sheet

(56) References Cited

PUBLICATIONS

Lambert et al.; Failure of Commercial Oral Amino Acid Supplements to Increase Serum Growth Hormone Concentrations in Male Body-Builders; International Journal of Sport Nutrition, 1993, 3, 298-305.

Legakis et al.; Human Galanin Secretion is Increased Upon Normal Exercise Test in Middle-Age Individuals; Endocrine Research 26(3), 357-365 (2000).

Maccario et al.; Relationships between IFG-I and age, gender, body mass, fat distribution, metabolic and hormonal variables in obese patients; International Journal of Obesity (1999) 23, 612-618.

Makimura et al.; The relationship between reduced testosterone, stimulated growth hormone secretion and increased carotid inima-media thickness in obese men; Clin Endocrinol (Oxf). Nov. 2010; 73(5): 622-629.

Menagh et al.; Growth Hormone Regulates the Balance Between Bone Formation and Bone Marrow Adiposity; JBMR; vol. 25, No. 4, Apr. 2010, pp. 757-768.

Merimee et al.; Arginine-Initiated Release of Human Growth Hormone; The New England Journal of Medicine; Jun. 26, 1969; pp. 1434-1438.

Nindl et al.; Growth hormone pulsatility profile characteristics following acute heavy resistance exercise; J. Appl Physiol 91: 163-172, 2001.

O'Connor et al.; Interrelationships of Spontaneous Growth Hormone Axis Activity, Body Fat, and Serum Lipids in Healthy Elderly Women and Men; Metabolism, vol. 48, No. 11 (November), 1999: pp. 1424-1431.

Papadakis et al.; Effect of growth hormone replacement on wound healing in healthy older men; Would Repair and Regeneration Oct.-Dec. 1996; pp. 421-425.

Papadakis et al.; Growth Hormone Replacement in Healthy Older Men Improves Body Composition but Not Functional Ability; Ann Intern Med. 1996; 124-: 708-716.

Pasquali et al.; Hormones and pathophysiology of obesity; Hormones and Obesity; 2001 pp. 9-20.

Pelsers et al.; Influence of Gender in Growth Hormone Status in Adults: Role of Urinary Growth Hormone; Clinical Chemistry 45, No. 3, 1999, pp. 443-444.

Perry, Horace M. III; The Endocrinology of Aging; Clinical Chemistry 45:8(B); 1369-1376 (1999).

Rubin et al.; New anabolic therapies in osteoporosis; Current Opinon in Reeumatology 2002, 14:433-440.

Rudman et al.; Effects of Human Growth Hormone in Men over 60 Years Old; The New England Journal of Medicine; vol. 323, Jul. 5, 1990; 6 pages.

Su et al.; Insulin-like growth factor 1 and hair growth; 1999 Dermatology Online Journal; 20 pages.

Suminski et al.; Acute Effect of Amino Acid Ingestion and Resistance Exercise on Plasma Growth Hormone Concentration in Young Men; International Journal of Sport Nutrition, 1997, 7, 48-60.

Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488, 2003.

Vance, Mary L.; Growth Hormone for the Elderly?; The New England Journal of Medicine; Jul. 5, 1990; pp. 52-54.

White et al.; Effects of an Oral Growth Hormone Secretagogue in Older Adults; J. Clin Endocrin Metab.; 2009; 29 pages.

Zouboulis et al.; Intrinsische Hautalterung; Eine kritische Bewertung der Rolle der Hormone; Hautarzt 2003 54: 825-832.

\* cited by examiner

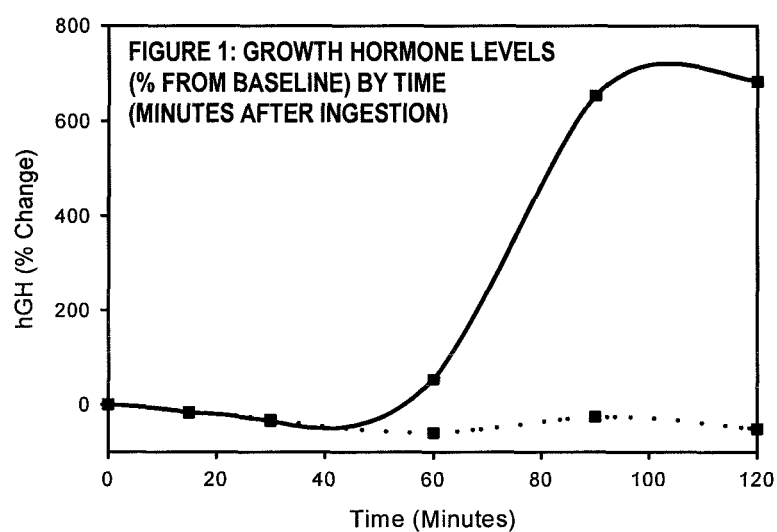

COMPOSITIONS FOR INCREASING HUMAN GROWTH HORMONE LEVELS

TECHNICAL FIELD

Embodiments of the invention generally relate to supplements for increasing human growth hormone (hGH) levels in healthy human beings.

BACKGROUND

The primary biological function of hGH includes stimulating growth, cell repair and regeneration. Once the primary growth period of adolescence concludes, the primary function of hGH in adulthood becomes that of cell regeneration and repair, helping regenerate skin, bones, heart, lungs, liver and kidneys to their optimal, youthful cell levels. As is the case with many of our other hormones or their pre-cursors, such as testosterone, oestrogen, progesterone, DHEA and melatonin, hGH levels decline with age. Therapeutically, many of these hormones can be replaced to offset some of the effects of aging such as menopausal symptoms in women or erectile dysfunction in men. The human body, like every other living entity, works on daily, or circadian, as well as monthly and annual rhythms. Daily growth hormone secretion diminishes with age with roughly half the levels at age forty that we had when we were twenty, and about one-third of those youthful levels at age sixty. In some sixty-year olds, the levels are as low as 25% of the hGH levels in a twenty-year old. Symptoms of aging include loss of muscle, increase of fat, decreased physical mobility, decreased energy levels and as a result, diminished socialization, diminished healing ability and an increased risk of cardiovascular disease and decreased life expectancy. Low hGH levels are associated with the aging process and early onset of disease. For example, Rosen and Bengtsson noted an increased death rate from cardiovascular disease in hGH deficient patients (Rosen, T., Bengtsson, B. A., Lancet 336 (1990): 285-2880).

Until recently human growth hormone (hereinafter alternatively referred to as hGH) was available only in expensive injectable forms, and benefits from the restoration of hGH levels available only to those with the ability to pay. Most recently substances that can trigger the release of human growth hormone from an individual's own anterior pituitary gland have become available. These are generically referred to as secretagogues. Secretagogues have the ability to restore hGH levels, potentially to the levels found in youth. See for reference the book entitled "Grow Young With hGH" by Dr. Ronald Klatz, President of the American Academy of Anti-Aging, published in 1997 by Harper Collins.

HGH-deficient adults have marked reductions in lean body mass, and within months of hGH treatment, gains in lean body mass, skin thickness and muscle mass are observed. (Cuneo R C et al. J Appl Physiol 1991; 70:695-700; Cuneo R C et al. J Appl Physiol 1991; 70:688-694; Rudman D et al. N Engl J Med 1969; 280:1434-1438).

It is well-established that intravenous (IV) administration of some amino acids results in significant hGH secretion. Intravenous infusion of 183 mg of arginine/kg body weight in females increased hGH levels>20-fold and 30 g of arginine elevated serum hGH levels 8.6 fold in males (Merimee T J et al. N Engl J Med 1969; 280:1434-1438; Alba-Roth J et al. J Clin Endocrinol Metab 1988; 67:1186-1189). Other amino acids, such as methionine, phenylalanine, lysine, histidine, and ornithine have also led to marked increases in hGH (Alba-Roth, Muller, Schopohl, & von Werder, 1988; Chromiak & Antonio, 2002; Gourmelen, M., M. Donnadieu, et al. (1972) Ann Endocrinol (Paris) 33(5): 526-528).

Given the difficulties in IV administration of amino acids for widespread use, interest in elucidating the hGH response to oral amino acid supplements prompted testing of such supplements containing mainly arginine, lysine and ornithine at varying amounts. Yet the pronounced variability in results among these studies, which differed in aspects including subject population, supplement composition, and dosage methodologies, make clear the complexities involved in the design of an effective supplement for supporting hGH levels in the general public. (Suminski R R et al. Int J Sport Nutr 1997; 7:48-60; Lambert M I et al. Int J Sport Nutr 1993; 3:298-305; Corpas E et al. J Gerontol 1993; 48:M128-M133; Isidori A et al. Curr Med Res Opin 1981; 7:475-481; Fogelholm G M et al. Int J Sport Nutr 1993; 3:290-297; Chromiak J A, Antonio J. Nutrition 2002 July; 18(7-8):657-61).

Thus determination of an effective and safe oral functional blend that stimulates hGH secretion in the general population is important to determine since athletes, entertainers and now the general public seek effective hGH support supplements and understand hGH to have rejuvenating properties.

Indeed, once partial to athletes and entertainers, the desire for effective supplements to provoke growth hormone (hGH) increases now extends to the general public. Not only do they have a goal of building lean tissue and reducing fat, but also in improving skin quality and other rejuvenating qualities that hGH is understood to provide. Despite proceeding literature on oral amino acids for use in stimulating hGH, evidence for an optimized oral amino acid-containing blend able to stimulate hGH in the general public including both men and women of a wide age range is not clear.

It would be desirable to provide a nutritional supplement for elevating hGH release, in particular an amino acid-containing composition that is well tolerated having the result of increasing or elevating hGH release in those individuals whose hGH release rates have slowed as a function of increasing age or that have normal hGH levels but desire higher hGH levels. Although some existing nutritional supplements claim to impact the production of natural human growth hormone, there is a need for an improved nutritional supplement that efficiently enhances the production and effect of natural human growth hormone in the general population.

BRIEF SUMMARY OF THE INVENTION

The present invention is a nutritional supplement. It is a novel amino acid-containing secretagogue composition, which, taken orally, stimulates the pituitary gland to increase serum levels of hGH.

A particular embodiment of the present disclosure relates to an oral nutritional supplement that includes the amino acids l-lysine, l-arginine, oxo-proline, and one of either cysteine or glutamine. The amino acids may be delivered as non-toxic salts thereof, effective complexes thereof, stable chelates thereof, active esters thereof, functional derivatives thereof, and mixtures thereof which are effective to increase hGH levels in the general population.

Another particular embodiment relates to an oral nutritional supplement that consists essentially of l-lysine HCl, l-arginine HCl, oxo-proline, N-acetyl-l-cysteine, l-glutamine, and schizonepeta (aerial parts) powder.

BRIEF DESCRIPTION OF THE FIGURES

FIG. 1 shows growth hormone levels after supplement administration compared to a placebo.

DETAILED DESCRIPTION OF THE INVENTION

The present invention relates to a nutritional supplement for use by a human being. The nutritional supplement is an amino acid-containing secretagogue composition, which, taken orally, stimulates the pituitary gland to increase serum levels of hGH. Increased levels of hGH may result in inhibition of insulin depression, inhibition of hyperglycaemia and increase in insulin effectiveness, enhancement of fat conversion, lowering of cholesterol, and normalization of lipid balance. The supplement of the present invention works as a dietary supplement by assisting the body's own ability to secrete hGH naturally in a manner that is safe and effective, as well as being affordable.

A particular embodiment of the present disclosure relates to an oral nutritional supplement that includes l-lysine, l-arginine, oxo-proline, and one of either cysteine or glutamine. The supplement may additionally include both cysteine and glutamine and/or schizonepeta powder. In particular embodiments, a functional dosage includes the l-arginine at a level between 0.1-6 mmol and the oxo-proline between 0.1-8 mmol, and/or the l-lysine in an amount between 0.1-12 mmol. The cysteine and/or glutamine may be contained at a level between 0.001-6 mmol. In another particular embodiment, a functional dosage includes the l-arginine HCl at a level between 2.5-4.5 mmol and the oxo-proline between 4-6 mmol, and/or the l-lysine HCl in an amount between 7-9 mmol The cysteine and/or glutamine may be contained at a level between 0.001-0.5 mmol. The cysteine can be n-acetyl L-cysteine and the glutamine may be l-glutamine. The amino acids may be delivered as non-toxic salts thereof, effective complexes thereof, stable chelates thereof, active esters thereof, functional derivatives thereof, and mixtures thereof which are effective, to increase hGH levels in the general population. The nutritional supplement may be present in an amount of 2.9 grams. The nutritional supplement may be in any acceptable and known oral formulation, such as powder, tablet, capsule, liquid, or wafer form.

Another particular embodiment relates to an oral nutritional supplement that consists essentially of l-lysine HCl, l-arginine HCl, oxo-proline, N-acetyl-l-cysteine, l-glutamine, and schizonepeta (aerial parts) powder. In particular embodiments, a functional dosage includes the l-arginine HCl at a level between 0.1-6 mmol and the oxo-proline between 0.1-8 mmol, and/or the l-lysine HCl in an amount between 0.1-12 mmol. The n-acetyl L-cysteine and/or l-glutamine may be contained at a level between 0.001-6 mmol. In another particular embodiment, a functional dosage includes the l-arginine HCl at a level between 2.5-4.5 mmol and the oxo-proline between 4-6 mmol, and/or the l-lysine HCl in an amount between 7-9 mmol. The n-acetyl L-cysteine and/or l-glutamine may be contained at a level between 0.001-0.5 mmol. The nutritional supplement may be in any acceptable and known oral formulation, such as powder, tablet, capsule, liquid, or wafer form.

Other embodiments are drawn to methods of increasing human growth hormone in humans that include orally administering the disclosed nutritional supplement to a healthy human being. As used herein, "healthy human being" means a human being without any physiological deficiency in hGH independent of age. Particular embodiments of the invention relate to oral administration of the disclosed nutritional supplement to a human that is at least 30 years old. The nutritional supplement may be administered from one to three times daily or, alternatively, may be administered every other day, or may be administered once a week. In particular embodiments, the nutritional supplement may be administered on an empty stomach.

In accordance with the "consist essentially of" and "consisting essentially of" language, the nutritional supplement of the third embodiments is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement of the present invention may be prepared in accordance with any method known to one of ordinary skill in the art. Alternatively, each ingredient may be obtained in a fully prepared from a commercially available source.

The nutritional supplement of the present invention may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement of the present invention may be ingested on a regular basis, such as a daily or weekly intake at a dosage tailored to an individual's needs; i.e., the nutritional supplement is to be taken regularly as multiples (1×, 2×, etc.) of the structural units (pills, tablets, capsules, liquid dose, etc.) in accordance with the needs of the individual. For example, a senior citizen leading a sedentary life may need higher daily doses than does a young person engaged in regular strenuous exercise (e.g., a weight lifter). Alternatively, the nutritional supplement of the present invention may be ingested on an as-needed basis at a dosage tailored to the individual's needs. Medical or nutritional counseling may be beneficial for arriving at a desirable or optimal dosage tailored to the individual's needs.

The combination of types of amino acids, mass ranges, and specific formulations have been selected to be synergistically balanced and of adequate quantity to achieve the desired physiological effect, namely, growth hormone release. Improper combinations of the amino acids may be ineffective. The component amino acids are synergistic in the sense that several of them when combined together, synergistically stimulate the release of human growth hormone. The combination was also chosen to reduce or inhibit chemical combination or reaction between the amino acids.

EXAMPLES

A cross-over, placebo controlled, double-blind study involved 16 healthy subjects [12 males, 4 females; 9 Caucasian, 6 African American, 1 other; mean age=32±14 years; body mass index=26.4±5.0 ranging from 19.1 to 36.8 kg/m$^2$]. Each subject reported to the Inpatient Unit on two occasions one week apart. After an overnight fast, subjects had an IV line placed and baseline bloods samples were drawn at −30, −15, and 0 minutes. Subjects were then asked to swallow the capsules of the test supplement or an identical looking placebo.

The administered supplement is a novel 2.9 g/dose blend of l-lysine HCl, l-arginine HCl, oxo-proline, N-acetyl-l-cysteine, l-glutamine, and schizonepeta (aerial parts) powder.

Blood was drawn at 15, 30, 60 and 90 and 120 minutes for assay. Human GH was measured at each time point using the Siemens Immulite 2000 (intra-assay CV was 3.72%, inter-assay CV was 5.70%, and the detection limit for GH was 0.05 ng/ml.

Mean growth hormone increased eight-fold over baseline (equivalent to 682%) after the supplement from 0.17 at baseline to 1.33 ng/ml at 120 minutes compared to a mean decrease of 52% after placebo from 0.93 to 0.45 ng/ml (FIG. 1). The mean change in GH levels from baseline to 120 minutes (GH at 120 minutes minus GH at 0 minutes), was 1.15 (95% CI: 0.17, 2.14) ng/ml after the supplement versus −0.48 (−1.47, 0.50) ng/ml after the placebo, demonstrating a statistically significant differential effect (P=0.01). After the supplement, the mean AUC for GH across 120 minutes was 20.43 (95% CI: 19.90, 20.95) ng/ml/min which was significantly higher (P=0.04) than placebo at 19.67 (18.74, 20.59) ng/ml/min. Overall, 120 minutes after taking the supplement, GH levels were significantly higher in both absolute levels and by AUC.

Mean levels of GH reached after the subcutaneous injection of 0.06 IU of HGH in the treatment of GH deficient subjects was 0.4 ng/ml, a value that was clearly in the range of values seen in our study with oral amino acids (Janssen Y J et al. *Br J Clin Pharmacol* 1999; 47:273-278).

The present study involved a broad range of ages and BMI's and included both genders. An additional advantage of this study of the amino-acid containing blend over previous hGH evaluations is that it contained a placebo control group and was randomized and double-blinded.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. An oral nutritional supplement consisting essentially of:
   about 1 mmol L-arginine;
   about 1 mmol Oxo-proline;
   about 2 mmol L-lysine;
   about 1.5 μmol N-acetyl L-cysteine; and
   about 125 μg Schizonepta (aerial parts) powder.

2. The supplement of claim 1, wherein the nutritional supplement is present in an amount of 2.9 grams.

3. An oral nutritional supplement consisting essentially of:
   3.44 mmol L-arginine;
   5.30 mmol Oxo-proline;
   8.21 mmol L-lysine;
   6.13 μmol N-acetyl L-cysteine;
   6.84 μmol L-glutamine; and
   0.50 mg Schizonepta (aerial parts) powder.

4. The supplement of claim 3, wherein the nutritional supplement is present in an amount of 2.9 grams.

5. The supplement of claim 3, wherein the nutritional supplement is in powder, tablet, capsule, liquid, or wafer form.

6. The supplement of claim 3, wherein the supplement consists of 725.50 mg L-arginine HCl; 683.70 mg L-pyroglutamic acid; 1499.30 mg L-lysine HCl; 1.00 mg N-acetyl L-cysteine USP; 1.00 mg L-glutamine; and 0.50 mg Schizonepta (aerial parts) powder.

* * * * *

UNITED STATES PATENT AND TRADEMARK OFFICE
CERTIFICATE OF CORRECTION

Page 1 of 1

PATENT NO. : 8,715,752 B2
APPLICATION NO. : 13/623117
DATED : May 6, 2014
INVENTOR(S) : Amy L. Heaton, Mitchell K. Friedlander and Dennis Gay It is certified that error appears in the above-identified patent and that said Letters Patent is hereby corrected as shown below:

On the title page:

In ITEM (72) Inventors:   change "Amy L Heaton," to --Amy L. Heaton,--
change "Mitchell K Friedlander," to
--Mitchell K. Friedlander,--

In ITEM (56) References Cited:
PUBLICATIONS, line 9   change "Volum" to --Volume--

Signed and Sealed this
Thirtieth Day of December, 2014

Michelle K. Lee
*Deputy Director of the United States Patent and Trademark Office*